(12) United States Patent
Cheng

(10) Patent No.: US 12,673,025 B2
(45) Date of Patent: Jul. 7, 2026

(54) PEGYLATED LIPOSOMES AND USES THEREOF

(71) Applicant: LT BIOPHARMA INC., Tainan City (TW)

(72) Inventor: Jya-Wei Cheng, Tainan City (TW)

(73) Assignee: LT BIOPHARMA INC., Tainan City (TW)

( * ) Notice: Subject to any disclaimer, the term of this patent is extended or adjusted under 35 U.S.C. 154(b) by 224 days.

(21) Appl. No.: 18/625,215

(22) Filed: Apr. 3, 2024

(65) Prior Publication Data

US 2025/0312277 A1     Oct. 9, 2025

(51) Int. Cl.
| | |
|---|---|
| *A61K 9/1271* | (2025.01) |
| *A61K 9/00* | (2006.01) |
| *A61K 38/16* | (2006.01) |
| *A61P 31/04* | (2006.01) |

(52) U.S. Cl.
CPC .......... *A61K 9/1271* (2013.01); *A61K 9/0019* (2013.01); *A61K 38/164* (2013.01); *A61P 31/04* (2018.01)

(58) Field of Classification Search
None
See application file for complete search history.

(56) References Cited

FOREIGN PATENT DOCUMENTS

CN          110612097 A  * 12/2019  ........... A61K 9/1271

OTHER PUBLICATIONS

Bacterial Infection, Cleveland Clinic, Accessed online Jan. 9, 2026).*

* cited by examiner

*Primary Examiner* — Melissa S Mercier
(74) *Attorney, Agent, or Firm* — Hannah Tien

(57) ABSTRACT

Provided herein are PEGylated liposomes, and methods of making and using thereof. The PEGylated liposomes comprise DSPE-peg2000 and nosiheptide in a molar ratio of 3:1. Compositions and methods which is related to making the PEGylated liposomes and using the PEGylated liposomes for preventing or treating bacterial infection are also provided.

12 Claims, 18 Drawing Sheets

Figure 1:
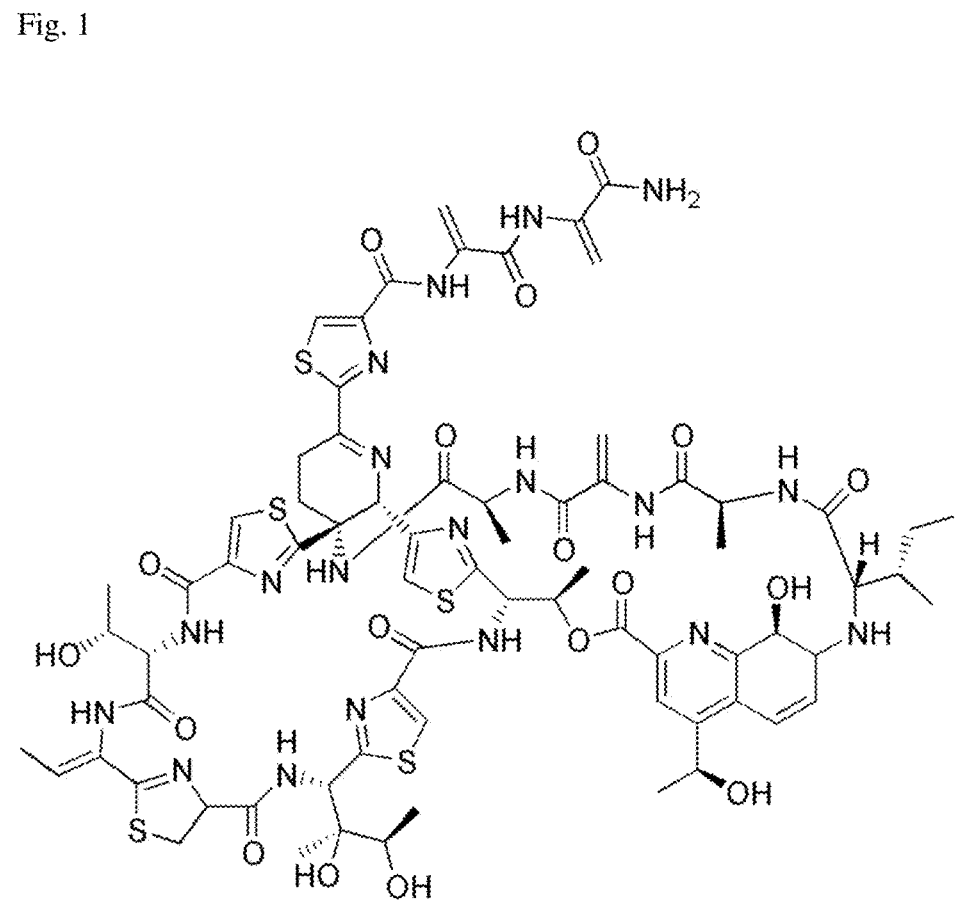

Figure 2:
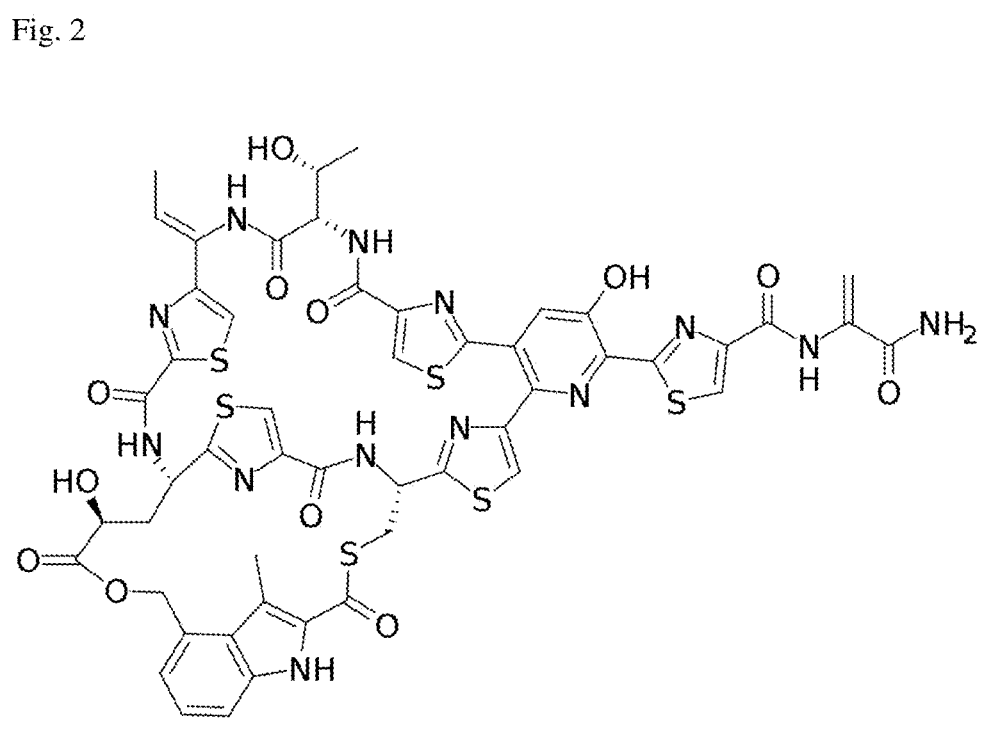

Figure 3:
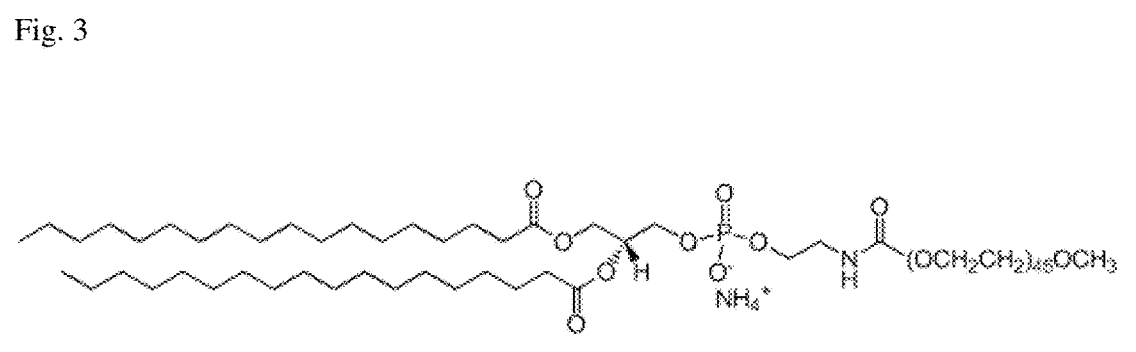

Thiostrepton Liposome Size Distribution

|  |  |  | Size (d.nm): | % Intensity: | St Dev (d.nm): |
|---|---|---|---|---|---|
| Z-Average (d.nm): | 129.7 | Peak 1: | 150.2 | 97.1 | 49.19 |
| Pdi: | 0.337 | Peak 2: | 5211 | 2.9 | 467.9 |
| Intercept: | 0.942 | Peak 3: | 0.000 | 0.0 | 0.000 |
| Result quality : | Good |  |  |  |  |

Nosiheptide Liposome Size Distribution

|  |  | Size (d.nm): | % Intensity: | St Dev (d.nm): |
|---|---|---|---|---|
| Z-Average (d.nm): 138.9 | Peak 1: | 173.6 | 100.0 | 60.73 |
| Pdi: 0.159 | Peak 2: | 0.000 | 0.0 | 0.000 |
| Intercept: 0.967 | Peak 3: | 0.000 | 0.0 | 0.000 |
| Result quality : Good |  |  |  |  |

FT-IR

PEGYLATED LIPOSOMES AND USES THEREOF

FIELD OF THE INVENTION

The present invention relates to PEGylated liposomes and methods of making and using thereof.

BACKGROUND OF THE INVENTION

Thiazolyl peptides, also known as thiopeptide antibiotics, are secondary metabolites produced by actinomycetes, thiostrepton and nosiheptide are one of the family members of this class of antibiotics, both of which are sulfur-containing, highly modified, macrocyclic peptides. These complex naturals are large cyclic peptide frameworks composed of modified heterocyclic residues such as thiazole, oxazole, and indole with dehydroamino acids. These special heterocyclic residues are active inhibitors of protein synthesis against Gram-positive bacteria. Moreover, several of thiazolyl peptides have other functions such as antifungal activity, anticancer agents, renin inhibitors, and even against *Plasmodium falciparum*, the malaria parasite. In addition, thiopeptide antibiotics have potent antimicrobial activity against drug-resistant strains of methicillin-resistant *Staphylococcus aureus* (MRSA). MRSA, which often cause fatal infections in humans, is the major cause of hospital-acquired infections that are becoming extremely difficult to defense due to emerging resistance to all current antibiotic classifications However, despite the efficacy against bacteria, the highly hydrophobic characteristics of thiazolyl peptides makes this class of antibiotics underestimated.

Thiostrepton (FIG. 1) is often referred to the parent compound of the thiopeptide antibiotics. Earliest isolated from *Streptomyces azureus*, this secondary metabolite is found to be potent against Gram-positive bacteria with activity compared with that of the penicillin. Nevertheless, in spite of a highly potential antibacterial characteristics, thiostrepton has not been developed for clinical use as resistance by the bacterium develops before the therapeutic dose be approached, mainly as a result of its extremely low solubility, which is the inherent problem with most of the thiopeptide antibiotics. Nevertheless, thiostrepton has previously been encapsulated in micelle nanocarriers (Esparza, K. and H. Onyuksel, *Development of co-solvent freeze-drying method for the encapsulation of water-insoluble thiostrepton in sterically stabilized micelles*. Int J Pharm, 2019. 556: p. 21-29). Despite the fact that the micelle-encapsulation indeed improved the solubility of thiostrepton and led an enhanced reduction in FOXM1 activity and cancer cell inhibition, the stability and the extremely low encapsulation efficiency are the disadvantage of micelle-encapsulation which have not settled in current.

Nosiheptide (FIG. 2), as a thiazole-containing polypeptide antibiotic with a distinctive indole side ring produced by the *Streptomyces actuosus*, is active against Gram-positive bacteria. However, Nosiheptide is never deeply developed as a human therapeutic.

Liposomes as drug carriers provide a biocompatible and effective therapeutic platform for the treatment of various diseases. The amphiphilic property of liposomes makes them ideal drug carriers for hydrophobic drugs. Liposomal encapsulated drugs can lower the toxicity, improve drug delivery efficiency for more effective anticancer and antibacterial treatments. Polyethylene glycol (PEG) is a biocompatible polymer that promotes blood circulation. PEGylated liposomes increase surface hydrophilicity, prolong drug circulation in the body, improve liposome drug delivery, and even reduce side effects.

Thin film hydration (FIG. 18) is the most common method applied for liposome synthesis (Large, D. E., et al., *Liposome composition in drug delivery design, synthesis, characterization, and clinical application*. Adv Drug Deliv Rev, 2021. 176: p. 113851). In this method, lipids and drug are uniformly solubilized and thoroughly mixed in miscible organic solvent. The mixture is then transferred into a round-bottom flask then the solvent is removed by using the rotary evaporator under vacuum, forming a thin film of lipids. Subsequently, the thin film is hydrated in desired solution. The hydrated temperature must be higher than the gel-liquid phase transition temperature (Tm) of the lipid. The final volume of the aqueous solution which used to hydration has an effect on the characteristics of the formed liposomes. After hydration, the multilamellar vesicles (MLVs) liposome is formed. Nonetheless, the rate of hydration determines the efficiency of drug encapsulation (Alavi, M., N. Karimi, and M. Safaei, *Application of Various Types of Liposomes in Drug Delivery Systems*. Adv Pharm Bull, 2017.7(1): p. 3-9).

Distearoylphosphatidylethanolamine-N-[methoxy (poly (ethyl eneglycol))-2000] (DSPE-peg2000) (FIG. 3), a representative PEGylated lipid, presents well biocompatibility while over the critical micellar concentration, DSPE-peg2000 molecules self-assembles as a monolayer in aqueous phase into a core-spherical structure with roughly 15 nm in diameter (Kastantin, M., et al., *Effect of the lipid chain melting transition on the stability of DSPE-PEG (2000) micelles*. Langmuir, 2009. 25 (13): p. 7279-86). The lipid core can load hydrophobic drugs as drug delivery system while the PEG core could increase solubility and protect the drug from biological degradation and elimination. 18-carbon acyl chains supply the DSPE-peg2000 molecules with a potent hydrophobic driving force for self-assembly into micelles, with a low critical micelle concentration value about 1 μM. The deeply low critical micelle concentration value makes the drug-loaded micelles stable upon the fast dilution that takes place when the drug is injected in blood vessels (Wu, F. G., J. J. Luo, and Z. W. Yu, *Infrared spectroscopy reveals the nonsynchronicity phenomenon in the glassy to fluid micellar transition of DSPE-PEG2000 aqueous dispersions*. Langmuir, 2010. 26(15): p. 12777-84).

However, despite the above, no clear formulation of PEGylated lipids as a nanodrug delivery system for thiazolyl peptides has been developed to date.

BRIEF DESCRIPTION OF THE DRAWINGS

FIG. 1: The structure of thiostrepton.

FIG. 2: The structure of nosiheptide.

FIG. 3: The structure of DSPE-peg2000.

SUMMARY OF THE INVENTION

Figure 4:
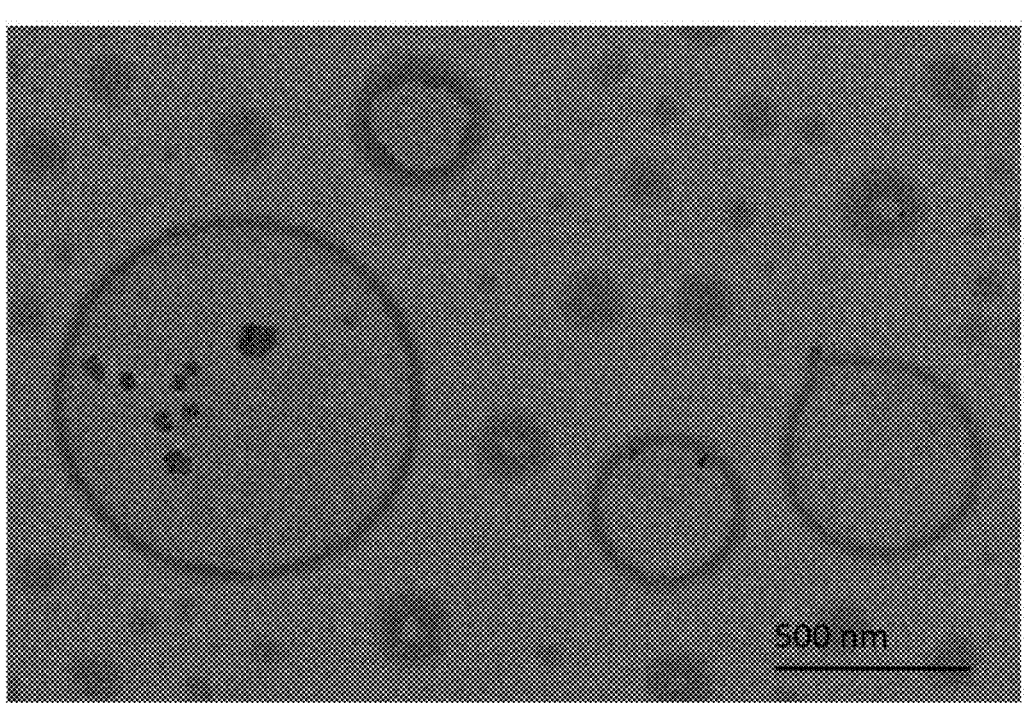
FIG. 4: The morphology of multilamellar vesicles which is captured while imaging nosiheptide liposome. Scale bar: 500 nm.
Figures 5A, 5B:
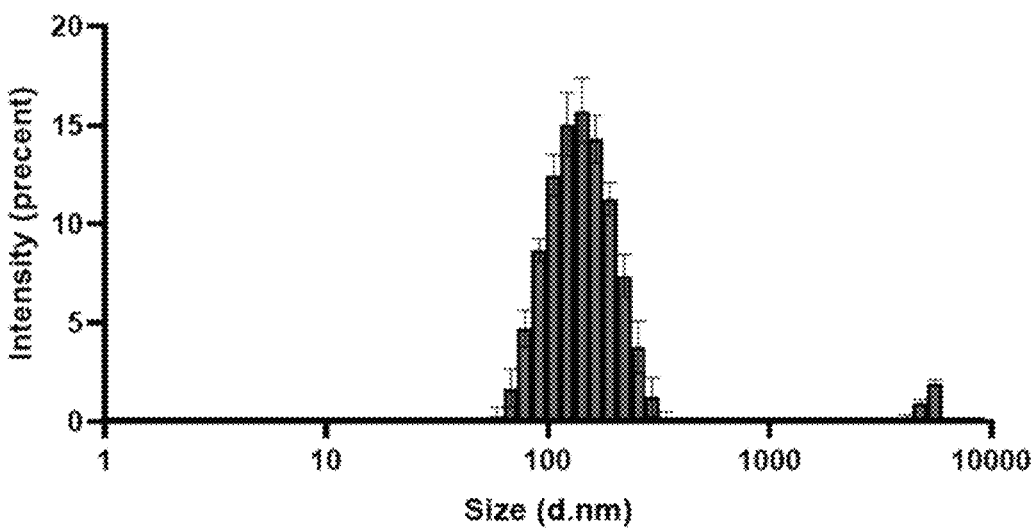
FIG. 5A: The size distribution of thiostrepton liposome measured by DLS.
FIG. 5B: A representative size distribution data of thiostrepton liposome. All data are conduct independently in triplicate, and all data are repeated in triplicate, and the data shown are the mean±S.D. from one representative experiment (n=3).
Figures 6A, 6B:
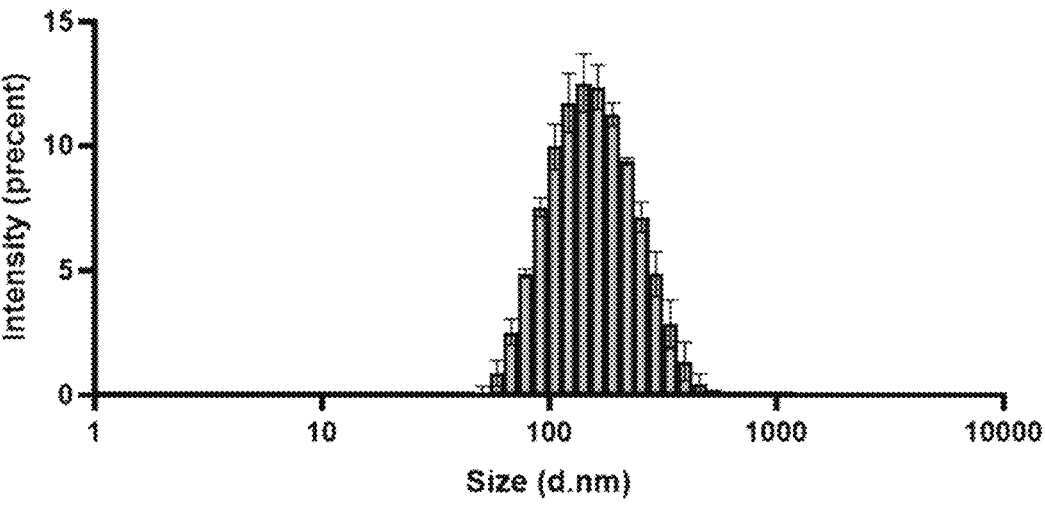
FIG. 6A: The size distribution of nosiheptide liposome measured by DLS.
FIG. 6B: A representative size distribution data of nosiheptide liposome. All data are conduct independently in triplicate, and all data are repeated in triplicate, and the data shown are the mean±S.D. from one representative experiment (n=3).

The present invention relates to a liposome comprising DSPE-peg2000 and nosiheptide, wherein the molar ratio of DSPE-peg2000:nosiheptide is 3:1. The present invention also relates to a pharmaceutical composition comprising the liposome of the present invention and a pharmaceutically acceptable carrier. The present invention further relates to a method for preventing or treating bacterial infection in a subject in need thereof comprising: administering to said subject a pharmaceutically effective amount of the composition of the present invention. The present invention still further relates to a method of preparing the liposome of the present invention comprising the steps of: a) dissolving DSPE-peg2000 in an organic solvent; b) dissolving nosiheptide in another organic solvent which is miscible with the solvent in step a; c) mixing the DSPE-peg2000 solution from step a and nosiheptide solution from step b with the molar ratio of DSPE-peg2000:nosiheptide equaling to 3:1; d) removing the solvent to form a thin film; e) hydrating the thin film in an aqueous medium to form multilamellar vesicles (MLVs) liposomes; and f) sonicating the MLVs solution whereby liposomes consisting of single unilamellar vesicles are obtained.

DETAILED DESCRIPTION OF THE INVENTION

In the present invention, liposomes are used as drug delivery system of thiazolyl peptides to improve their poor solubility and increase drug delivery efficiency, and the subsequent biocompatibility and activity tests are investigated. By using PEGylated lipids as drug carriers, a novel method to successfully prepared thiostrepton and nosiheptide liposomes with a particle size of around 150-200 nm is developed. In order to further confirm that the prepared liposomes are successfully loaded with drugs, fluorescence spectroscopy and infrared spectroscopy analysis are used, and the results show that the signals of thiostrepton and nosiheptide are observed in the liposomes.

To evaluate the effectiveness of liposomes as drug carriers, nosiheptide liposomes are used to test its stability, antimicrobial activity, cytotoxicity, hemolytic activity, and time-kill MICs. The results show that nosiheptide liposomes are effective against Vancomycin-Resistant *Staphylococcus aureus* (VRSA01), had potent antibacterial rate compared with free nosiheptide, almost no hemolytic activity in the hemolytic test, and relatively low cytotoxicity.

Overall, the results suggest that PEGylated lipid as drug carriers for thiostrepton and nosiheptide can effectively improve solubility. With high biocompatibility and rapid antibacterial efficacy, therefore, nosiheptide liposome can be a new type of antibacterial peptide against multi-drug resistant strains.

The PEGylated liposome-encapsulated nosiheptide according to the invention can be administered to patients parenterally or orally. Parenteral administrations include intravenous administration, intramuscular administration, subcutaneous administration, rectal administration, or percutaneous administration. Further, the PEGylated liposome encapsulated nosiheptide according to the invention may be formulated into a suitable dosage form depending upon the administration route. Examples of such dosage forms include, for example, injections used mainly, for example, for intravenous administration and intramuscular administration; external preparations for alternate parenteral administration, for example, eye drops, ear drops, nasal drops, ophthalmic ointments, skin mucosa absorbers, dermatologic preparations, inhalants, or suppositories; and preparations for oral administration, for example, capsules, tablets, pills, fine subtilase, granules, powders, syrups, or troches.

The term "treatment" or "treating" within the context of treating a bacterial infection means any treatment of any mammalian tissue that contains at least one bacterium that is not part of the normal flora and fauna of the mammal, or treatment of a mammalian tissue that is infected with bacterial infection in a mammal.

The term "effective amount" or "suitable amount" as used herein is at least the minimum concentration required to effect a measurable improvement or prevention of any symptom or a particular condition or disorder. The effective amount is thus dependent upon the specific biologically active molecule and the specific condition or disorder to be treated. Dosages for a particular individual patient can be determined by one of ordinary skill in the art using conventional considerations, (e.g. by means of an appropriate, conventional pharmacological protocol).

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "pharmaceutically acceptable carrier" as used herein refers to one or more compatible solid or liquid filler, diluents or encapsulating substances which are suitable for administration to a human or other subject contemplated by the disclosure. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers (e.g., antioxidants), gels, binders, excipients, disintegration agents, lubricants, sweetening agents, flavoring agents, dyes, such like materials and combinations thereof, as would be known to one of ordinary skill in the art.

The term "about" as used herein is intended to reflect a variation of 10% of the value it is attached to. For example, a concentration of "about 20%" is reflective of a concentration ranging from 18% to 22%. As another example, a quantity of "about $10^8$" is reflective of a range of $0.9 \times 10^8$ to $1.1 \times 10^8$.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

Therefore, the present invention provides a liposome comprising DSPE-peg2000 and nosiheptide, wherein the molar ratio of DSPE-peg2000:nosiheptide is 3:1. In an embodiment, the liposome is about 130 nm to 200 nm in diameter, and a polydispersity index of the liposome is less than 0.3.

The present invention also provides a pharmaceutical composition comprising a liposome comprising DSPE-peg2000 and nosiheptide with the molar ratio of 3:1 and a pharmaceutically acceptable carrier. In an embodiment, the liposome is about 130 nm to 200 nm in diameter, and a polydispersity index of the liposome is less than 0.3.

The present invention further provides a method for preventing or treating bacterial infection in a subject in need thereof comprising: administering to said subject a pharmaceutically effective amount of the composition comprising a liposome comprising DSPE-peg2000 and nosiheptide with the molar ratio of 3:1 and a pharmaceutically acceptable carrier. In an embodiment, the liposome is about 130 nm to 200 nm in diameter, and a polydispersity index of the liposome is less than 0.3. In an embodiment, the subject is a human. In an embodiment, the bacterial infection is caused by at least one strain of gram-positive bacteria, wherein the strain of gram-positive bacteria is selected from the group consisting of Vancomycin Resistant *Staphylococcus aureus* 01, *Staphylococcus aureus* ATCC29213, and *Staphylococcus aureus* ATCC33591. In an embodiment, the composition is administered via intravenous injection.

The present invention still further provides a method of preparing the liposome comprising DSPE-peg2000 and nosiheptide with the molar ratio of 3:1, which comprises the steps of: a) dissolving DSPE-peg2000 in an organic solvent; b) dissolving nosiheptide in another organic solvent which is miscible with the solvent in step a; c) mixing the DSPE-peg2000 solution from step a and nosiheptide solution from step b with the molar ratio of DSPE-peg2000:nosiheptide equaling to 3:1; d) removing the solvent to form a thin film; e) hydrating the thin film in an aqueous medium to form multilamellar vesicles (MLVs) liposomes; and f) sonicating the MLVs solution whereby liposomes consisting of single unilamellar vesicles are obtained. In an embodiment, the organic solvent in step a is methylene-chloride and the organic solvent in step b is dimethylformamide. In an embodiment, the aqueous medium in step e is phosphate buffer saline (PBS).

EXAMPLES

The examples below are non-limiting and are merely representative of various aspects and features of the present invention.

Example 1

Materials and Methods

Chemicals and Reagents

Nosiheptide was obtained from Sigma-Aldrich (St. Louis, MO, USA). Thiostrepton was purchased from Sigma-Aldrich (St. Louis, MO, USA). 1,2-distearoyl-sn-glycero-3-phosphoethanolamine-N-[amino (polyethyleneglycol)-2000] (ammonium salt) was purchased from Avanti Polar Lipids, Inc. (Alabaster, AL, USA). N,N-dimethylformamide (DMF) was purchased from Tedia Company Inc. (Tedia Way, Fairfield USA). Dichloromethane was purchased from JT Baker (Phillipsburg, New Jersey, USA). Ethanol was purchased from Echo Chemical Co., Ltd (Miaoli, Taiwan). Phosphate buffer saline (PBS) was made by the PBS buffer recipe, 1 L distilled $H_2O$ added with 8 g of NaCl and 0.2 g of KCl and 1.44 g of $Na_2HPO_4$ and 0.24 g of $KH_2PO_4$, adjusting the pH to 7.42. $H_2O$ used in all experiments was deionized to 18.2 MΩ (MILLIPORE).

Procedure of Liposomal Encapsulation

Liposome was prepared by thin film-hydration method. DSPE-peg2000 (6 mg, 6 mmol) was first dissolved in methylene-chloride. Nosiheptide (2 mg, 1.6 mmol) and thiostrepton (1 mg, 0.6 mmol) was dissolved in dimethyl-formamide, respectively. With the solvent dimethylforma-mide/methylene-chloride, lipid and nosiheptide were mixed with the molar ratio 3:1 in the round bottom flask; yet, lipid and thiostrepton were mixed with the molar ration 10:1. The organic phase was removed by rotary evaporator under water bath at 58° C. and 600 mmHg vacuum pressure. After dried the organic solvent, the thin-film was uniformly for-matted in the round bottom flask. In order to remove the organic solvent thoroughly, the thin-film was placed in 4° C. overnight. The residual thin-film was reconstituted by 2 ml PBS with the water bath at 45° C. While the thin-film dissolved in PBS, liposome was formatted multilamellar vesicles (FIG. 4). Then, the MLVs solution was sonicated (Misonix Sonicator 3000) for 10 minutes with 10 seconds pause 10 seconds on, at level 0.5 to let the MLVs fragment into single unilamellar vesicles (SUVs).

In order to separate liposome encapsulated thiazolyl pep-tides and free thiazolyl peptides, the SUVs solution passed through Sephadex G-25 (Pharmacia Biotech, Uppsala, Swe-den) gel filtration chromatography column (10×100 mm), the SUVs solution was loaded into a pre-equilibrated Sep-hadex G-25 column. Elution was performed with PBS buffer (pH 7.42) which containing 0.136 M NaCl, 2.68 mM KCl, 0.012 M $Na_2HPO_4$, and 1.76 mM $KH_2PO_4$, and the UV absorbance was measured at 310 nm for nosiheptide, at 300 nm for thiostrepton, individually. Fractions were collected and lyophilized and stored at −20° C. for further analysis. Dynamic Light Scattering (DLS) for Liposome Size Mea-surement The particle size distribution of nosiheptide liposome and thiostrepton liposome were analyzed by Malvern Zetasizer Nano ZS instrument (Malvern Instruments Ltd., Malvern, Worcestershire, UK). The mean hydrodynamic particle diameter was obtained from the Stokes-Einstein equation:

$$D = \frac{kT}{6\pi\eta R_H}$$

D: Diffusion coefficient
κ: Boltzmann's constant
T: Absolute temperature
η: viscosity
$R_H$: Hydrodynamic radius With the backscattering angle at 173°, η=0.8872 cP, T=25° C., refractive index=1.330, the liposomal hydrody-namic diameter was obtained. In order to ensure accuracy, each sample was measured in triplicate and each study was carried out in triplicate.
Determination of Concentration and Encapsulation Effi-ciency In an attempt to quantify the amount of nosiheptide in the liposome nanoparticles, first of all, the nosiheptide standard solution was prepared by the following steps: suitable amount of nosiheptide was dried by 55° C. drying oven for working standard, weighed accurately more than 20 mg, and dissolved in N, N-dimethylformamide (DMF) to prepare the nosiheptide standard stock solution with a concentration of 1 mg/ml. The nosiheptide standard solution with serial dilution were measured the UV absorbance at 310 nm by spectrophotometer (Ultraspec 2100 Pro, UV/Visible spectrophotometer, Biochrom, Massachusetts, USA) and estab-lished the calibration curve. In order to avoid the scattering of nanoparticle in optical measurement, the nosiheptide liposome solution was diluted serially by ethanol. The concentration of nosiheptide liposome was calculated with the concentration of nosiheptide standard solution. The process of determination of thiostrepton concentration was identical with above steps.

Encapsulation efficiency (EE %) was determined by col-umn method using Sephadex g-25 column (10×100 mm). 2000 μl nosiheptide liposome was loaded in the pre-equili-brated column with PBS and eluted with the same solution. Liposome encapsulated nosiheptide and free nosiheptide were collected respectively. Both nosiheptide encapsulated liposome ($C_{total}$) and free nosiheptide ($C_{free}$), collected from the Sephadex g-25 column, were determined by optical measurement after diluted with ethanol. The nosiheptide content in liposome was compared with the standard curve for the nosiheptide standard solution. The process of deter-mination of the encapsulation efficiency of thiostrepton liposome was identical with above steps. Percentages of encapsulation efficiency (EE %) were calculated as follow-ing equation:

$$EE(\%) = \frac{C_{total} - C_{free}}{C_{total}} \times 100\%$$

Characterization of Liposome Encapsulated Thiazolyl Pep-tides

The infrared transmission spectra of the prepared samples were measured at room temperature in the range 4000 $cm^{-1}$ to 450 $cm^{-1}$ at 2 $cm^{-1}$ resolution by an infrared spectrometer (Bruker, Vertex 80v) using a mid-infrared spectrometer fitted with an attenuated total reflectance (ATR) adapter (Spectrum 2, Perkin Elmer, Beaconsfield, UK). For infrared spectroscopy analysis, the powder of sample was completely dried at 55° C. oven to thoroughly remove water. Approxi-mately 5 mg of each sample were placed on the ATR crystal and the powder compressed until a reflection of 70% was obtained.

Fluorescence intensities were detected by a fluorescence spectrometer (Perkin Elmer LS55). The excited light source: Xenon discharge lamp, equivalent to 20 kW for 10 μs duration. The concentration of nosiheptide liposome and free nosiheptide were serially diluted form $2\times10^{-5}$ M. Fluo-rescence spectra were recorded in the range of 350 nm to 800 nm upon the excitation at 357 nm, the emission fluo-rescence of nosiheptide and nosiheptide liposome were obtained around 515 nm.
Bacteria Culture For the purpose of antimicrobial activity evaluation of liposome encapsulated nosiheptide, bacteria strain was cul-tivated in tryptic soy broth (Difco, Becton, Dickinson, Sparks, MD) or brain heart infusion broth (Difco, Becton, Dickinson, Sparks, MD) at 37° C. for 16~18 hours to the stationary phase. After that, 1000 μl of inoculums were treated to 15 ml tryptic soy broth medium and incubated at 37° C. for 3~4 hours. Bacteria counts were determined to $5\times10^5$ CFU/ml for antimicrobial activity via absorbance value of $OD_{600}$ (1 $OD_{600}=1\times10^8$ CFU/ml) by spectropho-tometer. (Ultraspec 2100 Pro, UV/Visible spectrophotom-eter, Biochrom, Massachusetts, USA)
Minimal Inhibitory Concentration (MIC) Assay The minimum inhibitory concentration values of peptides and liposome encapsulated peptides were evaluated by standard broth microdilution assay which was referred to the guideline of the Clinical and Laboratory Standards Institute (CLSI) (M27-A4., C.a.L.S.I.a.s.t.e.C.d., *Reference method for broth dilution antifungal susceptibility testing of yeasts.* Clinical and Laboratory Standards Institute, Wayne, PA., 2017). MIC assays were carried out with initial bacterial inoculum of $5 \times 10^5$ colony forming units (CFU/ml) in suitable medium. Peptides and liposome encapsulated peptides were added to polystyrene 96-well plates with serial dilution. Vancomycin-Resistant *Staphylococcus aureus* (VRSA01), *Staphylococcus aureus* (ATCC29213), *Staphylococcus aureus* (ATCC33591), *Pseudomonas aeruginosa* (ATCC278533) were cultivated in TSB broth. MICs was preliminarily defined as the lowest concentration of peptides which inhibited the 90% visible growth of bacteria.

The concentration-diluted peptide was treated 1 µl in 96-well plates. Subsequently, 99 µl medium which containing $5 \times 10^5$ CFU/ml bacteria inoculum were loaded individually in each wells, the serial-diluted concentration of peptide were from 8 to 0.0625 µg/ml. Evaluation of bacterial growth were performed by measuring the OD at 600 nm in a microplate reader (TECAN, Sunrise™) over 16 hours at 37° C. Medium-treated wells were used as the control, and all experiments were carried out in triplicate.

Time-Kill Analysis

The antimicrobial activity of nosiheptide and nosiheptide liposome against VRSA 01 were assessed by time-kill analysis. VRSA 01 was cultured in TSB medium overnight. After that, fresh TSB was inoculated for growth to mid-logarithmic phase. Bacteria was added at starting inoculum of $5 \times 10^9$ CFU/ml. Nosiheptide and nosiheptide liposome were added to final concentrations with $1 \times$MIC and $\frac{1}{4} \times$ MIC, the value of MICs were determined in previous experiments. Bacteria with only medium was regarded as the grown control. The cultures were incubated in 37° C. shaking incubator, and aliquots were removed from each tube at 1, 2, 4, 8, 24 hours and serially diluted for CFU enumeration on TSA plates. To compare rates of antibiotic killing, the decline of viable bacteria ($Log_{10}$ CFU/ml) was evaluated at the measured time points. Experiments were repeated independently in triplicate. The lower limit of detection for the colony counts was $2 \log_{10}$ CFU/ml.

Cell Viability

The MTT assay was performed to determine cell viability. $5 \times 10^3$ cells per well with 100 µl cell medium were plated in 96-well plates, incubating for 24 hours. Then, the cell medium in plates was removed and each well was treated medium with free nosiheptide or liposome encapsulated nosiheptide in serial-diluted concentration from 3.125 to 50 µM. The medium with PBS buffer was regarded as the control group. After incubating 24 hours, the medium was removed and 100 µl medium-diluted 10% MTT was added in the 96 well plate. After incubation for 3 hours, the MTT solution was removed and the residual formazan crystal was dissolved with 100 µl DMSO (Dimethyl sulfoxide, Sigma Aldrich). The cell viability was determined by measuring the absorbance at 570 nm using ELISA Reader (TECAN, Sunrise™), and the data was calculated by the following formula:

$$\text{Cell viability } \% = \frac{OD \text{ value(sample)} - OD \text{ value (Blank)}}{OD \text{ value (control)} - OD \text{ value (Blank)}} \times 100\%$$

The range of $IC_{50}$ values was obtained by observing the curve, and all experiments were carried out in triplicate.

Hemolysis Study

Hemolysis test was used to evaluate the safety of clinical use of nosiheptide and nosiheptide liposome. Erythrocytes were first collected in the venous blood collection tube (BD Vacutainer, REF 367525) from healthy blood donors. In order to thoroughly remove the serum in blood, human venous blood was washed three times with PBS buffer and were centrifuged at 4° C., 800×g for 10 minutes. Ultimately, the supernatant was removed and red blood cells were diluted by 10 times volume PBS buffer. The diluted red blood cells were incubated with equal volume nosiheptide and nosiheptide liposome, with the final concentration from 1.56 to 200 µg/ml, at 37° C. for 1 h. Yet, erythrocytes were treated with equal volume 1% Triton X-100 and PBS buffer as negative and positive control, respectively. Then, the incubated samples were centrifuged at 800×g for 5 minutes. The supernatant was collected for determination of the amount of hemoglobin, released from red blood cells, by measuring the absorbance at 405 nm using ELISA Reader (TECAN, Sunrise™). Data were express as percentage of hemolysis, and all experiments were implemented in triplicate.

Morphology of Nosiheptide Encapsulated Liposome

The morphology of liposomes was characterized by transmission electron microscopy (Hitachi HT7700, Hitachi Corporation, Tokyo, Japan). The sample was performed by drop casting method. A drop of the liposome solution was placed on the carbon-coated copper grid (EMS, Hatfield, PA), forming a thin liquid film. The films were negatively stained with 1% phosphotungstic acid (EMS, Hatfield, PA) solution (w/w; pH 7.2) for 1 minute. The excess of phosphotungstic solution was removed by filter paper. Samples were prepared with dyed or not respectively and were characterized by using an accelerating voltage of 100 kV.

In Vivo Study

Establishment of murine injection model of was assessed to test in vivo efficacy of nosiheptide liposome. Eight-week-old female ICR mice (LASCO, Taipei, Taiwan) were injected i.v. with $1 \times 10^9$ CFU/ml of *Staphylococcus aureus* (ATCC33591) strain in PBS buffer (pH=7.42). The mice were treated with nosiheptide liposome (20 mg/kg, 50 µl) and nosiheptide, as control, i.v. at 1 and 8 hours after bacteria inoculation and were observed for mortality and clinical status daily for 7 days.

Statistical Analysis

All data were performed at least three times. Evaluation of analyses were calculated and graphed by GraphPad Prism 8. All results are presented as means±SD. The comparisons were calculated by one-way ANOVA, Student's t-tests (two-tailed). Statistical significances were considered as *$p < 0.05$, $p < 0.01$, and *$p < 0.001$.

Results

Preparation of Liposomal-Encapsulation

Figure 17A:
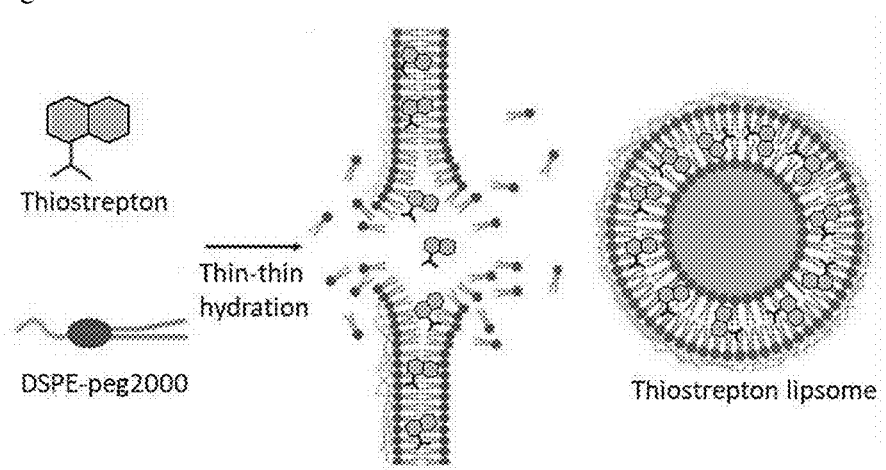
FIG. 17A: Schematic structure of liposome-encapsulated thiostrepton which thiostrepton molecules arrange between the lipid bilayers. Liposomes are composed by phospholipids, which share common amphiphilic structures of a polar head group and two hydrophobic alkyl tails. Phospholipids can self-resemble to form liposomes consisted of an aqueous core surrounded by lipid layers.
Figure 17B:
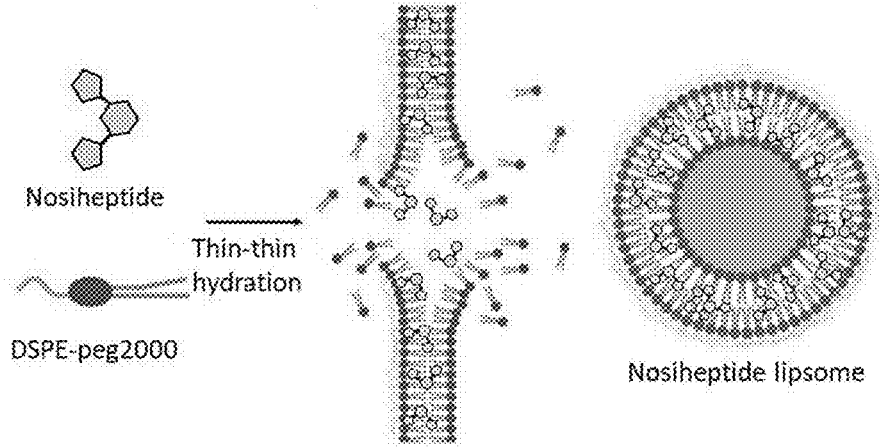
FIG. 17B: Schematic structure of liposome-encapsulated nosiheptide which nosiheptide molecules arrange between the lipid bilayers. Liposomes are composed by phospholipids, which share common amphiphilic structures of a polar head group and two hydrophobic alkyl tails. Phospholipids can self-resemble to form liposomes consisted of an aqueous core surrounded by lipid layers.
Figure 18:
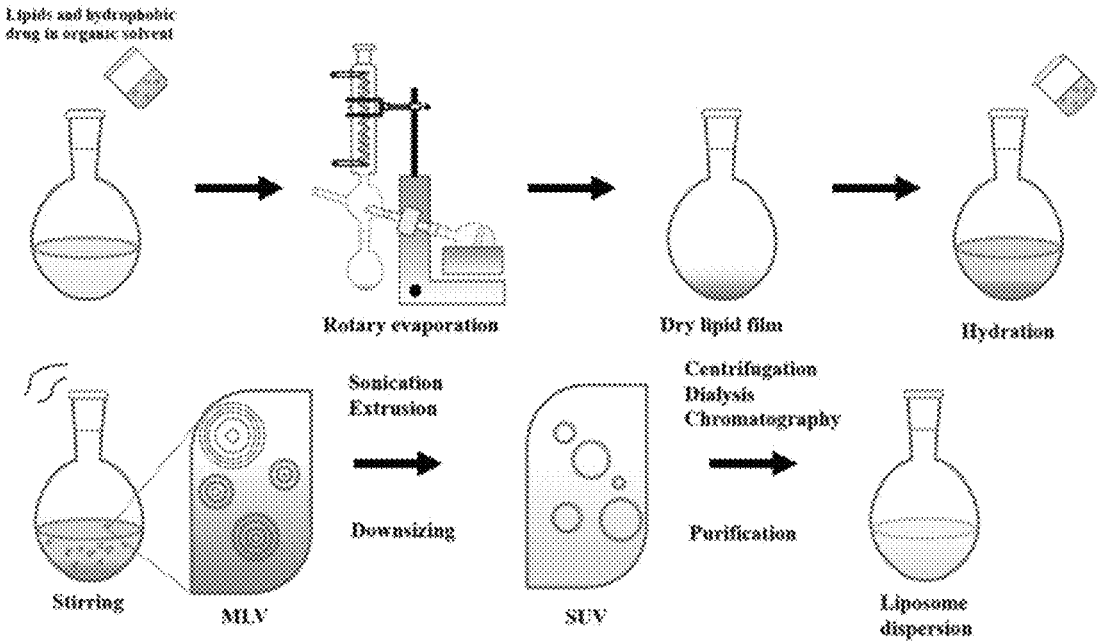
FIG. 18: Illustration of thin film hydration method.

Encapsulation of thiazolyl peptides into liposome was performed by using the thin film-hydration method (FIGS. 17A and 17B), and adjustment of the lipid to drug ratio optimized the liposome formulation and encapsulation condition. At concentrations above reported critical micelle concentrations (Kastantin, M., et al., *Effect of the lipid chain melting transition on the stability of DSPE-PEG (2000) micelles.* Langmuir, 2009. 25(13): p. 7279-86), various drug-to-lipid ratios were tested for their size distribution. The composition of liposome would test with the initial ratio of lipid to thiostrepton about 3:1, referred to the previously study (Wang, M. and A. L. Gartel, *Micelle-encapsulated*

*thiostrepton as an effective nanomedicine for inhibiting tumor growth and for suppressing FOXM1 in human xenografts.* Mol Cancer Ther, 2011. 10(12): p. 2287-97). With constant concentration of thiostrepton at 1 mg/ml, we changed the concentration of DSPE-peg2000 from 6 mg/ml to 10 mg/ml, the results found that the suitable size distribution of thiostrepton liposome was obtained from the lipid to peptide molar ratio in 10:1. In this ratio of composition, there was no significant precipitation in amount of thiostrepton encapsulated. As shown in Table 1, the distinguished formulation ratio of 10:1 DSPE-peg2000 to thiostrepton was chosen to be the ratio of liposome encapsulated thiostrepton for the following study.

TABLE 1

| | | Liposome encapsulation of thiostrepton and nosiheptide | | |
| Entry | Composition (molar ratio) | Size (nm) | PDI | EE(%) |
| --- | --- | --- | --- | --- |
| 1 | thiostrepton/DSPE-peg2000 = 1:3 | 443.6 | 0.112 | —[a] |
| 2 | thiostrepton/DSPE-peg2000 = 1:7 | 326.2 | 0.191 | — |
| 3[b] | thiostrepton/DSPE-peg2000 = 1:10 | 126.13 ± 3.88 | 0.38 ± 0.05 | 69.1 ± 6 |
| 4 | nosiheptide/DSPE-peg2000 = 1:2 | 209.4 | 0.308 | 32.1 |
| 5[c] | nosiheptide/DSPE-peg2000 = 1:3 | 139.83 ± 3.97 | 0.18 ± 0.01 | 54.7 ± 4.2 |
| 6 | nosiheptide/DSPE-peg2000 = 1:7 | 80.14[a] | 0.629 | — |
| 7 | DSPE-peg2000[e] | 111.20 ± 3.29 | 0.30 ± 0.01 | — |

[a]No conduct this experiment.
[b]The chosen thiostrepton liposome composition for further experiment
[c]The chosen nosiheptide liposome composition for further experiment
[d]Two distribution group: 17.74 nm (19.3%), 191.2 nm (80.7%)
[e]The lipid-only empty liposome Likewise, with constant concentration of nosiheptide at 2 mg/ml, we changed the concentration of DSPE-peg2000 from 4.5 mg/ml to 15 mg/ml, the result was found that the suitable size distribution was obtained from the lipid to drug molar ratio in 3:1, after which there was no significant precipitation in amount of nosiheptide encapsulated. As shown in Table 1, the optimal formulation ratio with 3:1 DSPE-peg2000 to nosiheptide was chosen to be the ratio of liposome encapsulated nosiheptide for the following study.

Size Distribution and Stability Study

The size distribution was assessed to explore preliminarily the characterization of liposome. Liposome encapsulated thiazolyl peptides which used the thin-film hydration with the mentioned ratio of the lipid to peptide were performed for all set of experiments resulting values of mean diameter around 130 nm. With respect to the lipid only liposome formulation, the DSPE-peg2000 liposome size range presented the value of mean diameter around 111.20±3.29 nm. In addition, the size range of liposome encapsulated nosiheptide and liposome encapsulated thiostrepton were presented the mean diameter around 139.83±3.97 nm and 126.13±3.88 nm, respectively (FIGS. 5A, 5B, 6A and 6B).

Figure 7A:
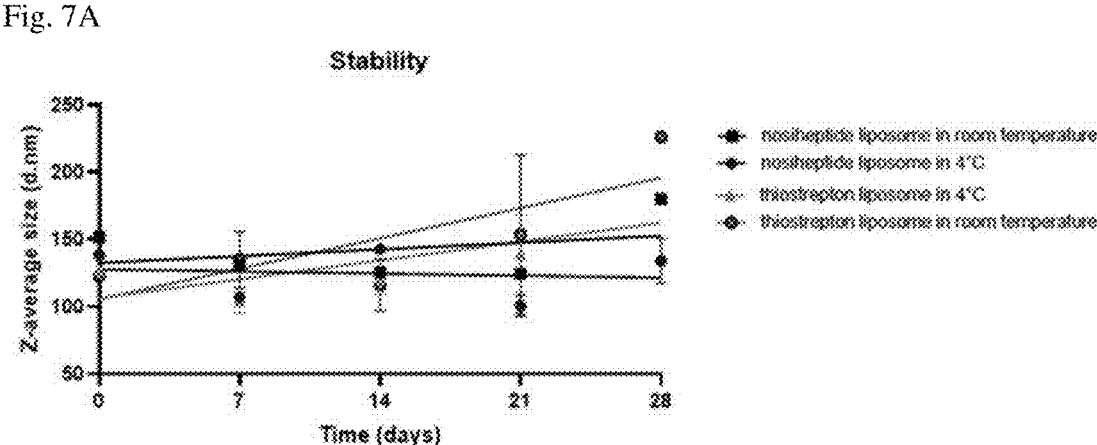
FIG. 7A: The stability test of nosiheptide liposome and thiostrepton liposome carries out at 4° C. and room temperature, respectively.
Figure 7B:
FIG. 7B: Nosiheptide liposome size before and after lyophilization (n=3). All data are conduct independently in triplicate, and all data are repeated in triplicate, and the data shown are the mean±S.D. from one representative experiment (n=3).
Figure 7B:
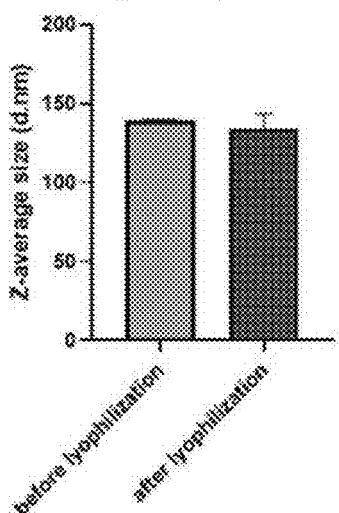

The stability study was carried out on liposome encapsulated thiazolyl peptides over a period of 4 weeks. Two different storage conditions, room temperature and 4° C. respectively, were selected to observe the variation of vesicle size during storage. Experiment results were shown the similar performance in same condition. As shown in FIG. 7A, in the beginning two weeks storage, slight size differences about 10 nm were observed in all experimental conditions. However, both liposome encapsulated nosiheptide and thiostrepton storage at room temperature were shown dramatically increased size changing after two weeks. Compared to the condition of storage at room temperature, liposome encapsulated thiostrepton storage at 4° C. had gradually increasing size changing about 50 nm were observed over the storage time. In addition, the particle size of liposome encapsulated nosiheptide before and after lyophilization was almost the same (FIG. 7B). Generally, lyophilization could be the suitable storage method for liposome encapsulated thiazolyl peptides.

Characterization of Liposome Encapsulated Thiazolyl Peptides

Figure 8:
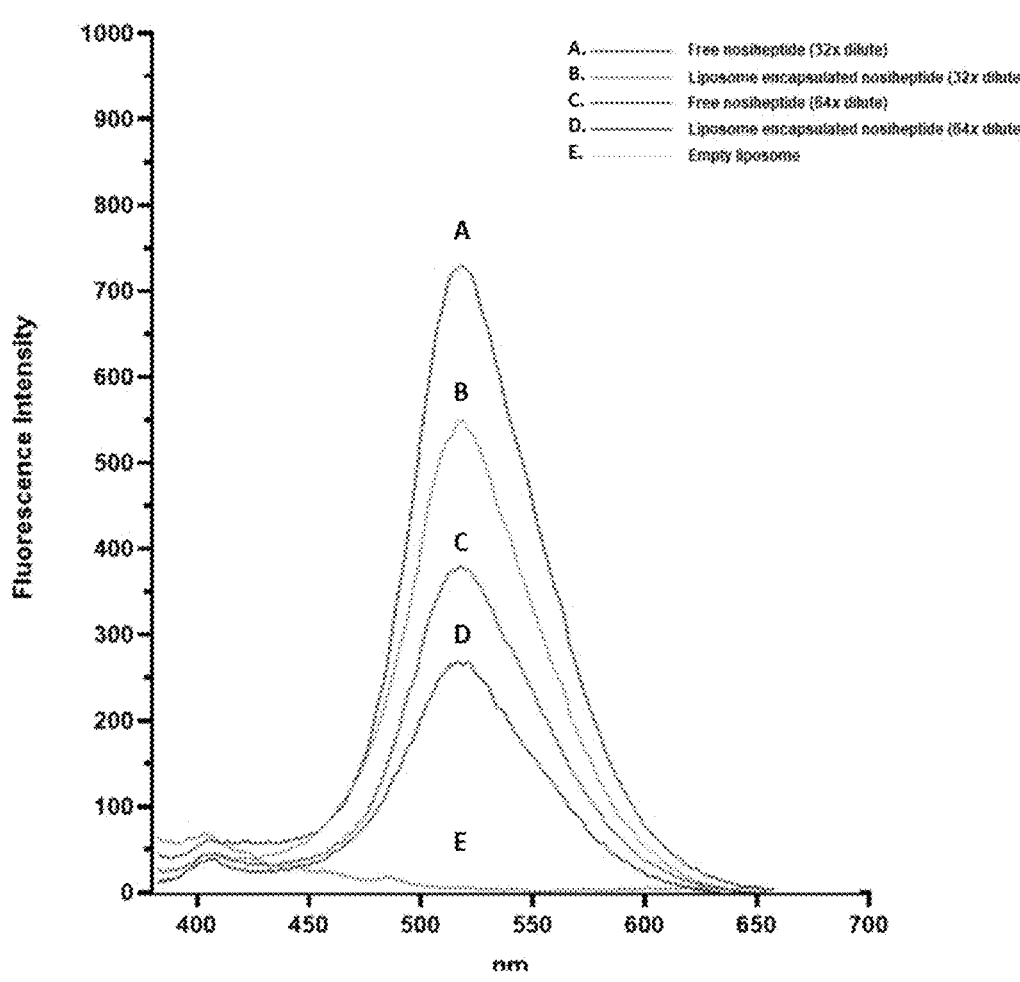
FIG. 8: The fluorescence spectrum of nosiheptide liposome. The fluorescence spectrum of nosiheptide and nosiheptide liposome which are diluted by EtOH at different dilution ratio from 32-fold to 64-fold.

Due to the fluorescence property of nosiheptide, fluorescence emission spectra was conducted by measuring the fluorescence intensity originated from nosiheptide. Fluorescence emission spectra was measured for free nosiheptide and nosiheptide liposome solution, using ethanol as diluted solvent. With an excitation wavelength at 357 nm, the fluorescence spectra of free nosiheptide and nosiheptide liposome appeared emission signals around 515 nm. As shown in FIG. 8, the fluorescence of the nosiheptide vesicle solution and free nosiheptide with different concentrations was measured. Result indicated that both free nosiheptide and nosiheptide liposome appeared the emission wavelength around 515 nm, the lipid only liposome showed no fluorescent signal. In addition, at same concentration of free nosiheptide and nosiheptide liposome, free nosiheptide had stronger emission than nosiheptide liposome.

FT-IR spectrum (FIG. 9 and FIG. 10) was conducted to observe the major functional groups and molecular interaction between the components in the drug carriers. For lipid only liposome, as shown in figure, there were several IR bands mainly originating from the transmittance of the PEG part in this wavenumber region: the $CH_2$ wagging vibration ($\omega CH_2$, ~1359 cm$^{-1}$), the CH2 twisting vibrations ($\tau CH_2$, ~1279 cm$^{-1}$ and ~1239 cm$^{-1}$), and the C—O—C stretching vibration ($\nu C$—O—C, ~1105 cm$^{-1}$) (Wu, F. G., J. J. Luo, and Z. W. Yu, *Infrared spectroscopy reveals the nonsynchronicity phenomenon in the glassy to fluid micellar transition of DSPE-PEG2000 aqueous dispersions.* Langmuir, 2010. 26(15): p. 12777-84). As for the peptide, nosiheptide, there were several IR bands mainly arising from the transmittance of the amide bond in this wavenumber region: the symmetric $NH_2$ stretching ($vNH_2$, ~3377 cm$^{-1}$), and the C=O stretching vibration ($vC$=O, ~1656 cm$^{-1}$) (Fabian, H. and C. P. Schultz, *Fourier Transform Infrared Spectroscopy in Peptide and Protein Analysis, in Encyclopedia of Analytical Chemistry*. 2006). The infrared spectra of nosiheptide liposome retained some of the characteristics of nosiheptide and DSPE-peg2000. With the wavenumber region: The C=O stretching vibration ($vC$=O, ~1642 cm$^{-1}$), the CH$_2$ wagging vibration ($\omega CH_2$, ~1343 cm$^{-1}$), the CH$_2$ twisting vibrations ($\tau CH_2$, ~1239 cm$^{-1}$ and ~1213 cm$^{-1}$), and the C—O—C stretching vibration ($vC$—O—C, ~1045 cm$^{-1}$).

Figure 9:
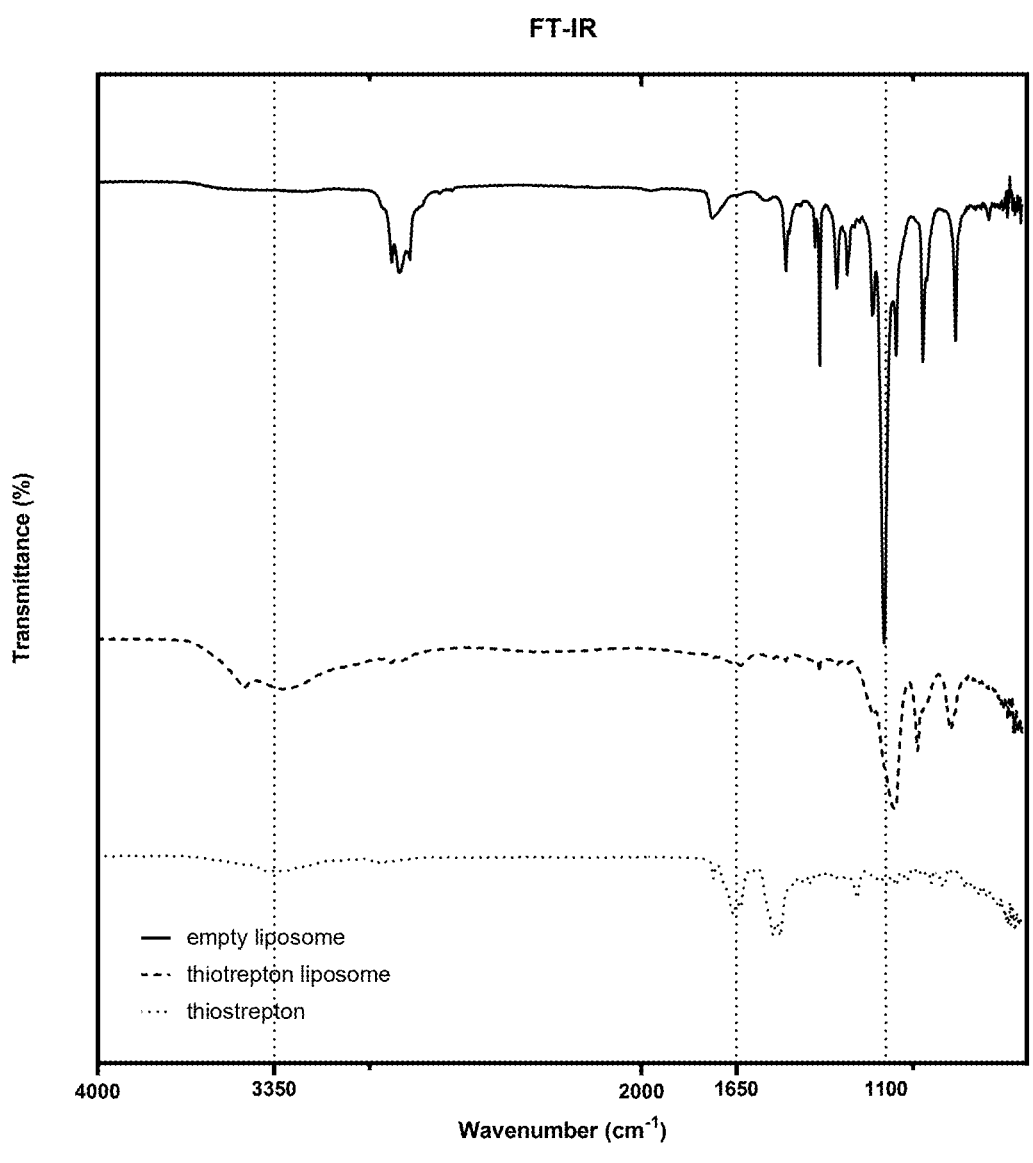
FIG. 9: FT-IR spectra of thiostrepton liposome compared with free thiostrepton and DSPE-peg2000.

In addition, the infrared spectrum of thiostrepton, shown as FIG. 9, indicated some IR bands mainly resulted from the transmittance of the amide bond in this wavenumber region: the symmetric NH$_2$ stretching ($vNH_2$, ~3376 cm$^{-1}$), and the C=O stretching vibration ($vC$=O, ~1660 cm$^{-1}$ and ~1635 cm$^{-1}$). The infrared spectra of thiostrepton liposome remained parts of the characteristics of thiostrepton and DSPE-peg2000. With the wavenumber region: the symmetric NH$_2$ stretching ($vNH_2$, ~3462 cm$^{-1}$), the C=O stretchthiostrepton. For initial study, the MIC in the range of 8 µg/ml to 0.625 µg/ml (8, 4, 2, 1, 0.5, 0.25, 0.125, 0.0625 µg/mL) of all peptides or liposome encapsulated peptides with 24 hours incubation was tested.

As shown in Table 2, nosiheptide liposome was performed potent antimicrobial activity against Vancomycin-Resistant *Staphylococcus aureus* (VRSA01), *Staphylococcus aureus* (ATCC29213), *Staphylococcus aureus* (ATCC33591), the MICs value were in the range of 0.25-0.125 µg/ml, which were 2-fold higher than free nosiheptide. Nonetheless, both free nosiheptide and nosiheptide liposome were shown no antibacterial activity against *Staphylococcus aureus* (ATCC19636), *Pseudomonas aeruginosa* (ATCC278533)

Besides, thiostrepton liposome was shown relatively weak antimicrobial activity against Vancomycin-Resistant *Staphylococcus aureus* (VRSA01), *Staphylococcus aureus* (ATCC29213), *Staphylococcus aureus* (ATCC33591). The MICs value all were 1 µg/ml, which were 5-fold higher than free thiostrepton. Similarly, both free thiostrepton and thiostrepton liposome were shown no antibacterial activity against *Staphylococcus aureus* (ATCC19636), *Pseudomonas aeruginosa* (ATCC278533)

TABLE 2

The MIC values of liposome encapsulated thiazolyl peptides and free thiazolyl peptide

Figure 10:
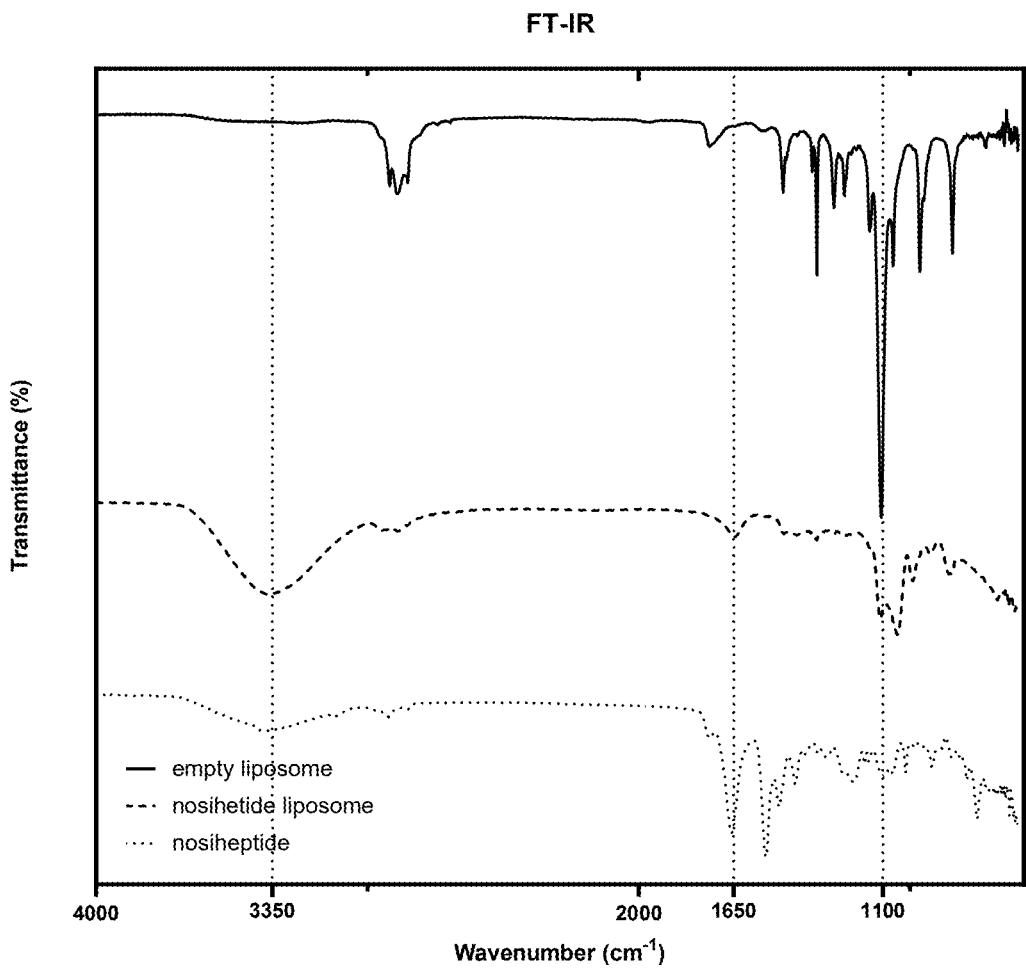
FIG. 10: FT-IR spectra of nosiheptide liposome compared with free nosiheptide and DSPE-peg2000. A broad strong band at 3360 cm-1 is for nosiheptide liposome. This band can be logically assigned to a hydroxyl group OH stretching vibration. The residual H2O by the material led to the presence of the OH band in IR spectrum.

| Bacterial strains | MIC (µg/ml) | | | | |
| --- | --- | --- | --- | --- | --- |
| | Nosiheptide Free | Nosiheptide Liposome | Thiostrepton Free | Thiostrepton Liposome | Empty Liposome |
| Vancomycin Resistant *Staphylococcus aureus* 01 | 0.0625 | 0.125 | 0.25 | 1 | 1 |
| *Staphylococcus aureus* ATCC29213 | 0.125 | 0.25 | 0.625 | 1 | 1 |
| *Staphylococcus aureus* ATCC33591 | 0.0625 | 0.125 | 0.625 | 1 | 1 |
| *Staphylococcus aureus* ATCC19636 | >8 | >8 | >8 | >8 | 8 |
| *Pseudomonas aeruginosa* ATCC 27853 | >8 | >8 | >8 | >8 | 8 | ing vibration ($vC$=O, ~1658 cm$^{-1}$ and ~1633 cm$^{-1}$), the CH$_2$ wagging vibration ($\omega CH_2$, ~1344 cm), the CH$_2$ twisting vibrations ($\tau CH_2$, ~1279 cm$^{-1}$ and ~1241 cm$^{-1}$), and the C—O—C stretching vibration ($vC$—O—C, ~1065 cm$^{-1}$). Due to the interaction of thiazolyl peptides and lipid, the characteristic bands of nosiheptide liposome or thiostrepton liposome in IR spectrum were slightly shifted. However, FIG. 10 showed a broad strong band at 3360 cm$^{-1}$ for nosiheptide liposome. This band could be theoretically assigned to the hydroxyl group OH stretching vibration. The residual H$_2$O by the material led to the presence of the OH band in infrared spectra.

In Vitro Antimicrobial Activity

The MIC test of nosiheptide liposome and thiostrepton liposome were conducted against the growth of Vancomycin-Resistant *Staphylococcus aureus* (VRSA01), *Staphylococcus aureus* (ATCC29213), *Staphylococcus aureus* (ATCC33591), *Staphylococcus aureus* (ATCC19636), and gram-negative bacteria *Pseudomonas aeruginosa* (ATCC278533), and compared with free nosiheptide and All data was carried out in triplicate.

Time-Kill Kinetics of Nosiheptide and Nosiheptide Liposome

Figure 11:
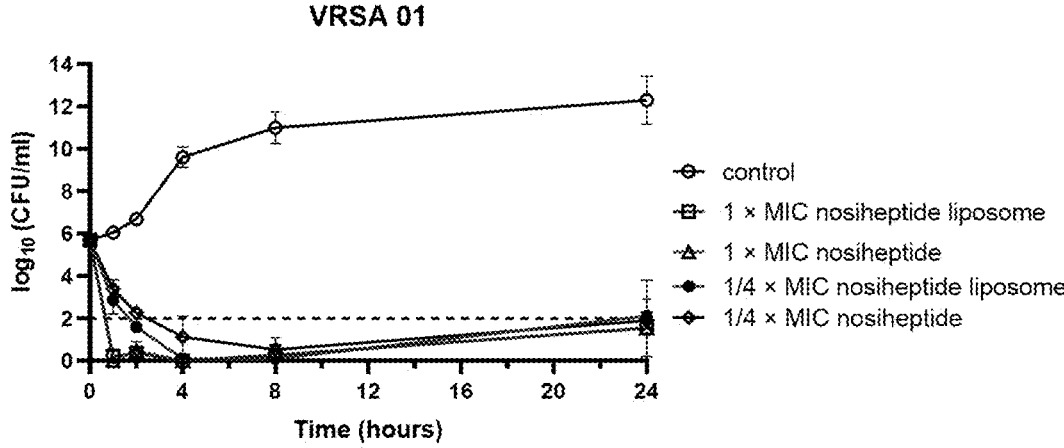
FIG. 11: Time-kill analysis against VRSA 01. Nosiheptide liposome and free nosiheptide killing kinetics is studied against VRSA at multiples of their MICs (MIC=0.125 µg/ml for nosiheptide liposome, MIC=0.0625 µg/ml for nosiheptide). The lower limit of detection for the colony counts is 2 log 10 CFU/ml. All data is repeated in triplicate, and the data shown are the mean±S.D. from one representative experiment (n=3).

In vitro time-kill analysis was used to evaluate nosiheptide killing kinetics activity against Vancomycin-Resistant *Staphylococcus aureus* (VRSA01). As shown in FIG. 11, both free nosiheptide and nosiheptide liposome had rapidly bactericidal against VRSA 01 in time-dependent manner. Both nosiheptide (0.0625 µg/ml) and nosiheptide liposome (0.125 µg/ml) at 1×MIC performed under 2-log kill noted within 1 hour. At ¼×MIC, nosiheptide liposome exhibited rapid antibacterial activity, with a nearly 2-log kill noted within 2 hours, while free nosiheptide presented much slower, reducing the initial inoculum to 2-log kill until 4 hours. Although both free nosiheptide and nosiheptide liposome demonstrated strong bactericidal activity against VRSA 01 at 1×MIC within 8 hours, the inoculum was still observed under 2-log unit at 24 hours. From the result, it was found that nosiheptide liposome had more rapid bactericidal against VRSA than free nosiheptide in time-dependent manner.

In Vitro Cell Viability and Hemolysis Study

Figure 12:
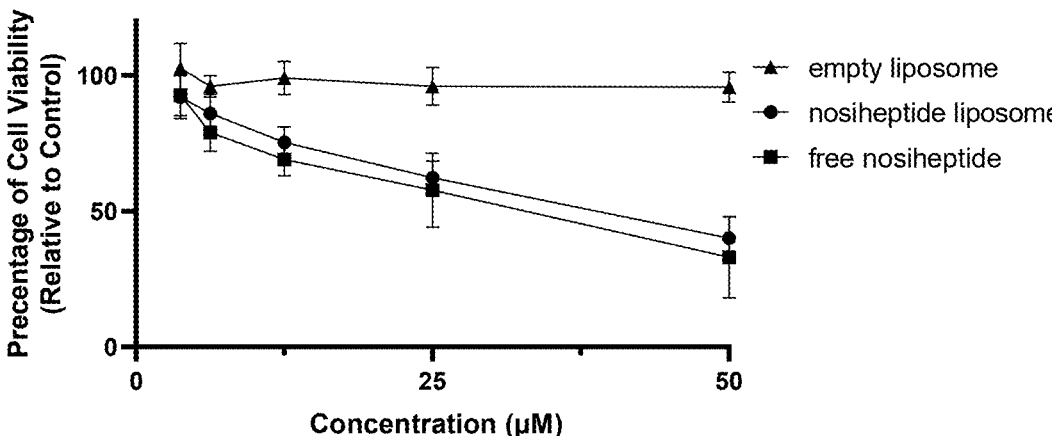
FIG. 12: The effects of nosiheptide liposome, free nosiheptide, and liposome only control (as empty liposome particles), on the cell viability of HFW cells after 24 h treatment. All data are conducted in triplicate, and each assay is repeated in triplicate, and the data shown are the mean±S.D. from one representative experiment (n=3).
Figure 13:
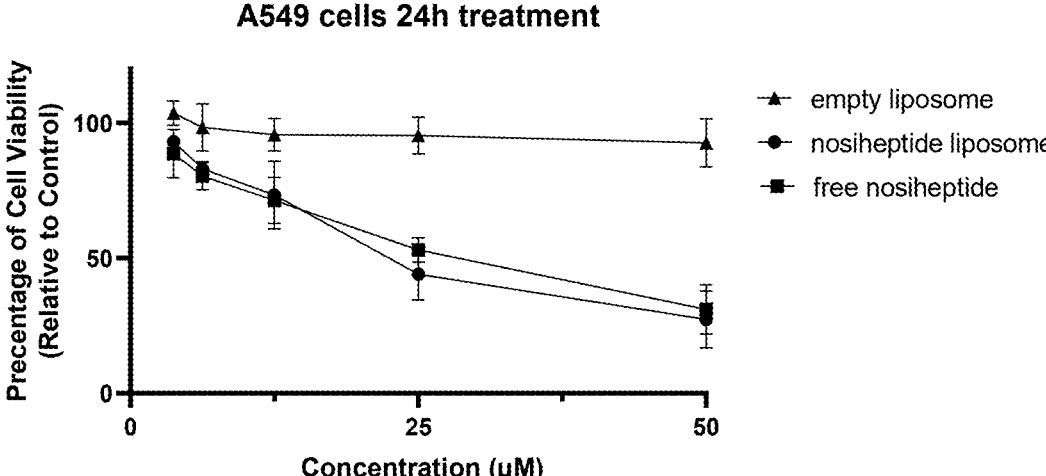
FIG. 13: The effects of nosiheptide liposome, free nosiheptide, and liposome only control (as empty liposome particles), on the cell viability of A549 cells after 24 h treatment. All data are conducted in triplicate, each assay is repeated in triplicate, and the data shown are the mean±S.D. from one representative experiment (n=3).

The comparative cell viability of nosiheptide and nosiheptide liposome were conducted using MTT assay. Treated to the normal cell, HWF cells, with serial-diluted concentration from 3.125 to 50 μM, the half maximal inhibitory concentration (IC$_{50}$) of nosiheptide and nosiheptide liposome were 28.31±9.23 μM and 36.29±7.99 μM, respectively (FIG. 12). In addition, treated to the lung cancer cells, A549 cells, with serial-diluted concentration from 3.125 to 50 μM, the IC$_{50}$ of nosiheptide and nosiheptide liposome were 26.22±5.26 μM and 23.04±4.37 μM, individually (FIG. 13). The results revealed that liposome encapsulation can slightly increase the inhibitory effect of nosiheptide treated to A549 cells compared with free nosiheptide, which suggested the potential of nosiheptide liposome for anticancer. Moreover, while treating to HFW cells, nosiheptide liposome could somewhat lower the cytotoxicity in contrast to free nosiheptide.

Figure 14:
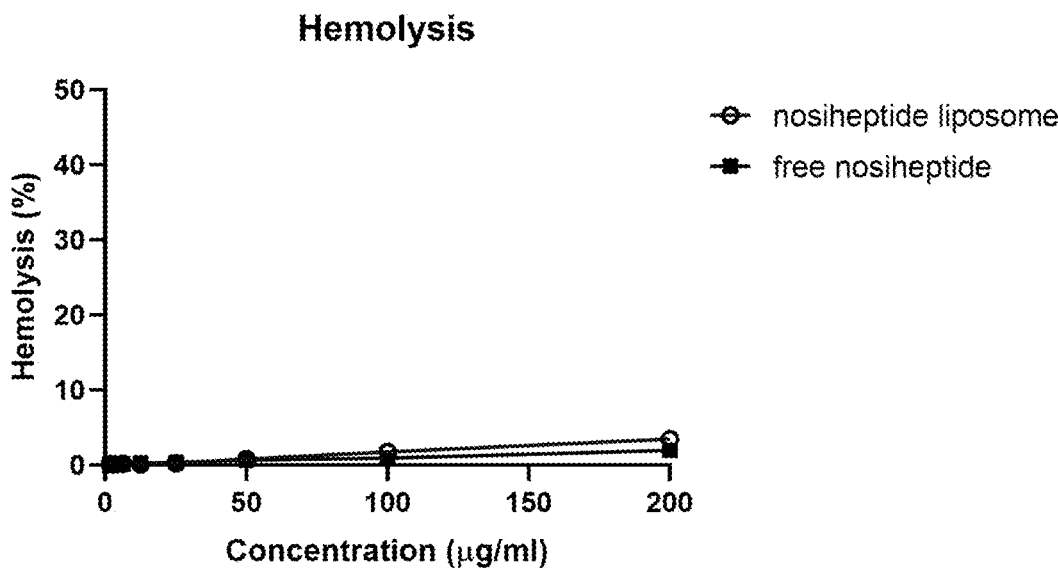
FIG. 14: Hemolytic activity study of nosiheptide liposome formulation at different nosiheptide concentration. Free nosiheptide in DMSO are used as control for comparison. Hemolytic activity study using human RBCs with nosiheptide liposome formulation and free nosiheptide, after 1 h incubation. All data are conducted in triplicate, and the data shown are the mean±S.D. from one representative experiment (n=3).

To confirm the biocompatibility of the liposome encapsulated nosiheptide, the hemolytic activity of nosiheptide liposome toward human red blood cells were evaluated with serial concentration from 200 μg/ml to 1.56 μg/ml. To quantify the hemolysis rate, 1% Triton X-100 and PBS were used as positive and negative controls, respectively. As shown in FIG. 14, both nosiheptide and nosiheptide performed nearly no hemolytic activity, even at 200 μg/ml the hemolysis of nosiheptide and nosiheptide liposome was less than 5%. Free nosiheptide, dissolved in DMSO, was used as control for comparison which showed slightly lower toxicity than the liposome encapsulated nosiheptide.

Morphological Characterization of Nosiheptide Liposome

Figure 15:
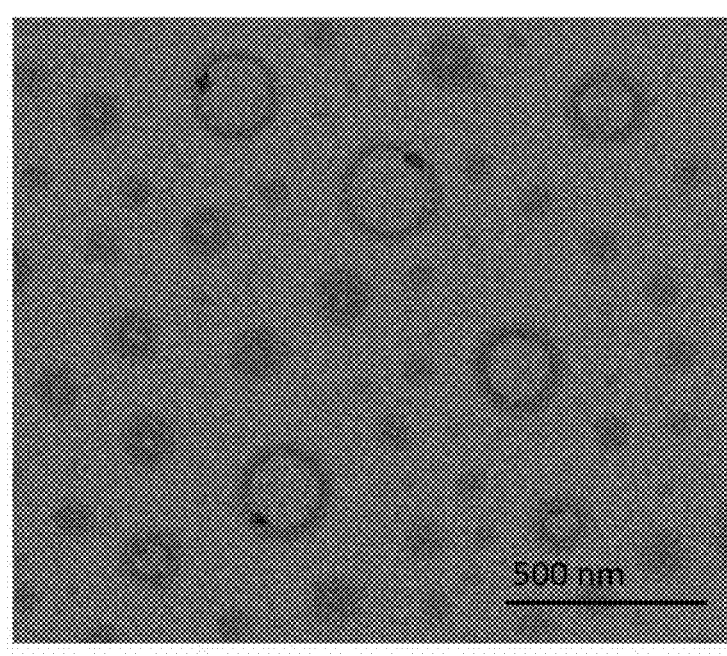
FIG. 15: The morphology of nosiheptide liposome. A representative TEM image of nosiheptide liposome. Scale bar: 500 nm.

The morphology of nosiheptide liposome was imaged by Transmission electron microscope (TEM). As shown in FIG. 15, no-stained images revealed that nosiheptide liposome was a typically spherical vesicle structure with well-dispersed single particles. According to TEM images, liposomes ranged in size from 100 to 200 nm with serval multilamellar vesicles. Indeed, microscopic size results were correlated well with the size values obtained by DLS, revealed average nosiheptide liposome size as approximately 150 nm with a narrow distribution. Additionally, the drop casting method performed no impact on liposome morphological characteristics. There had no crystallization of liposome observed in TEM images.

In Vivo Efficacy of Nosiheptide Liposome

Figure 16:
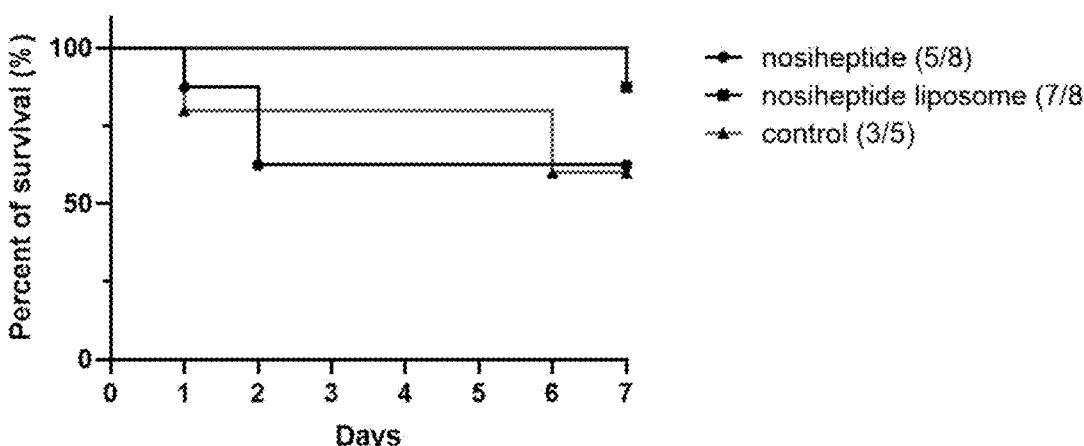
FIG. 16: The survival of mice (n=8 per group) which are infected i.v. with *S. aureus*, followed by i.v. treatment with nosiheptide and nosiheptide liposome (20 mg/kg) or vehicle control at 1 hour and 8 hours after infection. N=8 mice per treatment group, control group n=5, yet.

Due to its potent activities against *Staphylococcus aureus* in vitro, nosiheptide liposome and nosiheptide was tested in a murine model of i.v. *S. aureus* infection. Mice were infected with *Staphylococcus aureus* (ATCC33591), followed by nosiheptide liposome and nosiheptide treatment (20 mg/kg, i.v.) at 1 and 8 hours after infection. In FIG. 16, during the first two days of the experiment, ⅜ of the nosiheptide-treated mice died, ⅕ of the controls died on day one, whereas none of the nosiheptide liposome-treated mice died. In the end of the study, only one mouse in the nosiheptide liposome group had died, and the survival rate of nosiheptide liposome, nosiheptide, and control were 87.5%, 62.5%, 60%, respectively. These results indicated the evidence of well in vivo activity for nosiheptide liposome, i.e., the liposomal encapsulation formulation optimized the nosiheptide delivery in vivo.

One skilled in the art readily appreciates that the present invention is well adapted to carry out the objects and obtain the ends and advantages mentioned, as well as those inherent therein. The liposomes, preparing methods and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A liposome comprising Distearoylphosphatidylethanolamine-N-[methoxy(poly(ethyleneglycol))-2000] (DSPE-peg2000) and nosiheptide, wherein the molar ratio of DSPE-peg2000:nosiheptide is 3:1.

2. The liposome of claim 1, which is about 130 nm to 200 nm in diameter.

3. The liposome of claim 1, wherein a polydispersity index of the liposome is less than 0.3.

4. A pharmaceutical composition comprising the liposome of claim 1 and a pharmaceutically acceptable carrier.

5. A method for treating bacterial infection in a subject in need thereof comprising: administering to said subject a pharmaceutically effective amount of the composition of claim 4.

6. The method of claim 5, wherein the subject is a human.

7. The method of claim 5, wherein the bacterial infection is caused by at least one strain of gram-positive bacteria.

8. The method of claim 7, wherein the strain of gram-positive bacteria is selected from the group consisting of Vancomycin Resistant *Staphylococcus aureus* 01, *Staphylococcus aureus* ATCC29213, and *Staphylococcus aureus* ATCC33591.

9. The method of claim 5, wherein the composition is administered via intravenous injection.

10. A method of preparing the liposome of claim 1 comprising the steps of: a) dissolving DSPE-peg2000 in an organic solvent; b) dissolving nosiheptide in another organic solvent which is miscible with the solvent in step a; c) mixing the DSPE-peg2000 solution from step a and nosiheptide solution from step b with the molar ratio of DSPE-peg2000:nosiheptide equaling to 3:1; d) removing the solvent to form a thin film; e) hydrating the thin film in an aqueous medium to form multilamellar vesicles (MLVs)

liposomes; and f) sonicating the MLVs solution whereby liposomes consisting of single unilamellar vesicles are obtained.

11. The method of claim 10, wherein the organic solvent in step a is methylene-chloride and the organic solvent in step b is dimethylformamide.

12. The method of claim 10, wherein the aqueous medium in step e is phosphate buffer saline (PBS).

\*  \*  \*  \*  \*